United States Patent [19]

Gehrmann et al.

[11] 4,016,048
[45] Apr. 5, 1977

[54] DISTILLATIVE PURIFICATION OF 2,5-DIOXO-1-OXA-2-PHOSPHOLANES

[75] Inventors: Klaus Gehrmann, Erftstadt-Lechenich; Alexander Ohorodnik, Erftstadt-Liblar; Elmar Lohmar, Rodenkirchen; Wernfried Riechmann, Bruhl, all of Germany

[73] Assignee: Hoechst Aktiengesellschaft, Frankfurt am Main, Germany

[22] Filed: July 13, 1976

[21] Appl. No.: 704,774

[30] Foreign Application Priority Data

July 17, 1975 Germany .......................... 2531920

[52] U.S. Cl. .................................. 203/49; 203/72; 203/80; 203/89; 203/100; 260/545 P
[51] Int. Cl.² ...................... B01D 3/28; B01D 3/34; C07F 9/02
[58] Field of Search ................. 203/49, 72, 80, 89, 203/96, 92, 100; 260/545 P

[56] References Cited

UNITED STATES PATENTS

| | | | |
|---|---|---|---|
| 3,476,656 | 11/1969 | Van Tassell et al. ................. | 203/49 |
| 3,591,666 | 7/1971 | Pellegrini et al. .................... | 203/49 |

FOREIGN PATENTS OR APPLICATIONS

| | | | |
|---|---|---|---|
| 1,208,291 | 1/1966 | Germany .......................... | 203/89 |
| 187,780 | 10/1966 | U.S.S.R. ........................... | 260/545 P |

Primary Examiner—Wilbur L. Bascomb, Jr.
Attorney, Agent, or Firm—Connolly and Hutz

[57] ABSTRACT

2,5 dioxo-1-oxa-2-phospholanes of the general formula:

$$R^1-P(O)-O-CO-CHR^3-CHR^2$$

in which $R^1$ stands for an alkyl radical having from 1 to 4 carbon atoms, or a phenyl radical, and $R^2$ and $R^3$ each stand for hydrogen or $CH_3$, are distillatively purified. To this end the respective crude compound is preheated to 120° to 160° C and fed to the head of a distilling column provided with a plurality of individually heatable trays maintained at temperatures increasing from the upper-most tray to the lowermost, the uppermost tray in the column being maintained at 120° to 160° C and the lowermost tray being maintained at 160° to 200° C, the pressure at the head of the column being 20 to 200 mm Hg, preferably 50 to 120 mm Hg; an inert gas preheated to 160° to 200° C is introduced countercurrently at the base of the column; those impurities having a boiling point lower than that of the respective 2,5-dioxo-1-oxa-2-phospholane are withdrawn overhead together with the inert gas; the 2,5-dioxo-1-oxa-2-phospholane thus freed from low-boiling impurities is withdrawn from the base of the distilling column and passed to a film evaporator; and the 2,5-dioxo-1-oxa-2-phospholane is distilled off from higher-boiling impurities in the film evaporator under a pressure of 0.1 to 5 mm Hg.

4 Claims, 1 Drawing Figure

U.S. Patent  April 5, 1977  4,016,048
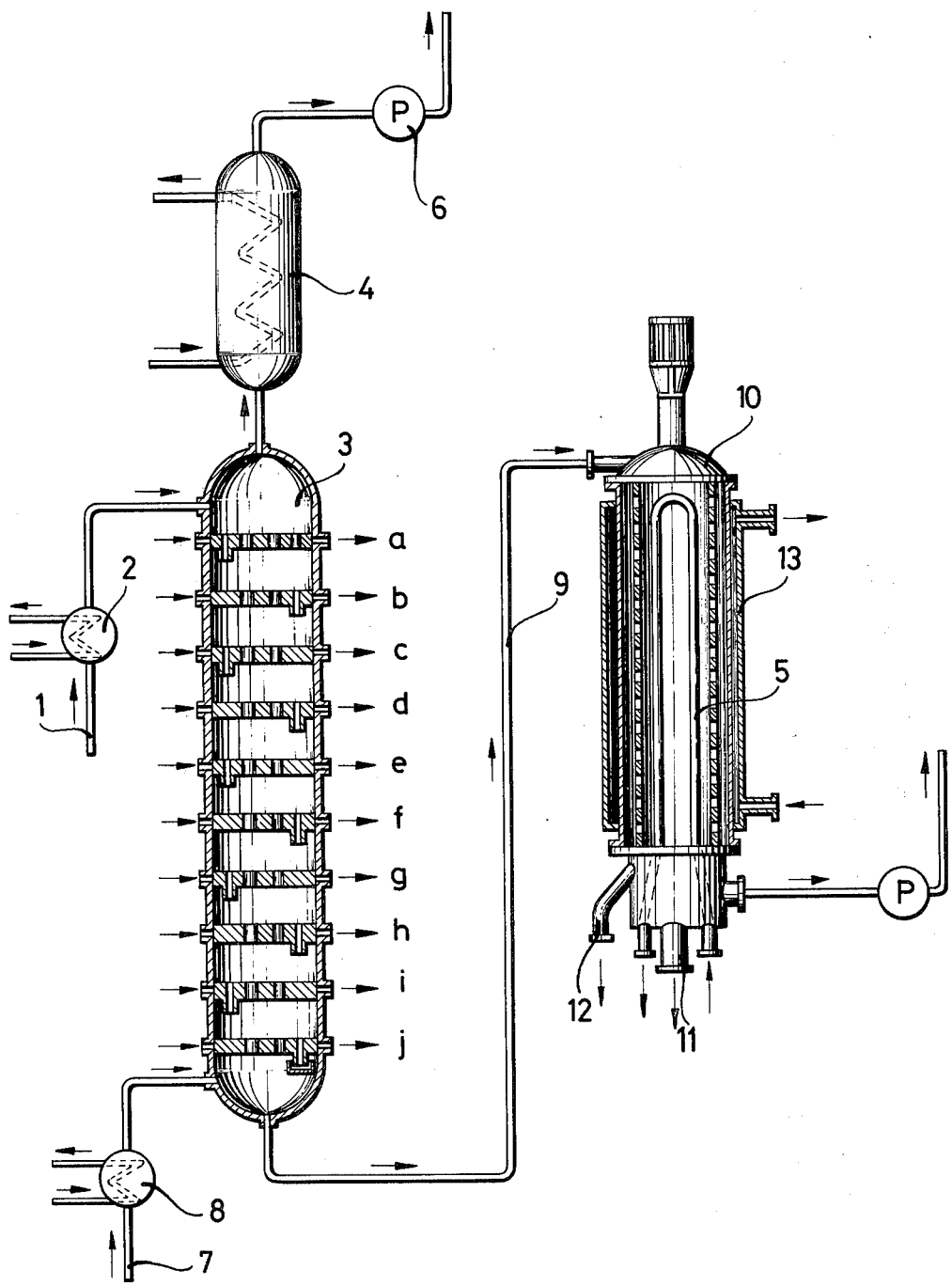

DISTILLATIVE PURIFICATION OF 2,5-DIOXO-1-OXA-2-PHOSPHOLANES

This invention relates to the distillative purification of 2,5-dioxo-1-oxa-2-phospholanes of the formula

in which $R^1$ stands for an alkyl radical having 1, 2, 3 or 4 carbon atoms, or a phenyl radical, and $R^2$ and $R^3$ each stand for hydrogen or $CH_3$.

One of the advantageous uses of 2,5-dioxo-1-oxa-2-phospholanes, which are obtainable, for example, by reacting beta-halogenoformyl-ethyl phosphinic acid halides with acetic anhydride, is their condensation with polyester forming reactants with a view to the production of filaments, fibres, sheets or articles having particularly good flame-retardant or self-extinguishing properties (cf. German Pat. ("Offenlegungsschrift") No. 2346787). 2-ethyl-2,5-dioxo-1-oxa-2-phospholane, for example, can also be made by a somewhat different process which comprises reacting ethyldichlorophosphine with a mixture of acrylic acid and methacrylic acid (Z.Obsc. Chim. 42 (1972), pages 1730-1733).

2,5-dioxo-1-oxa-2-phospholanes, insofar as they are to be incorporated as acid components in polyester molecules, need to be extremely pure. The presence of even minor impurities therein has been found to adversely affect the quality of the resulting polycondensates, which are liable to have an undesirable coloration or an undesirably low molecular weight, due to premature chain termination. In addition to this, the impurities may well affect adversely the course of the polyester-forming reaction, and may entail longer condensation periods or reduce space-time yields. This is the reason why 2,5-dioxo-1-oxa-2-phospholanes containing less than 0.1 weight % of impurities are almost exclusively used for condensation with polyester forming reactants.

2,5-dioxo-1-oxa-2-phospholanes have a high boiling point and are very reactive compounds, which can therefore not be purified by ordinary methods. 2-methyl-2,5-dioxo-1-oxa-2-phospholane is the lowest-boiling of these phospholanes, with a boiling point of 150° C under 0.5 mm Hg. Even at approximately 200° C, however, this compound undergoes thermal decomposition, which occurs the more rapidly the lower the purity of the compound.

In view of this it is easy to understand why very pure 2,5-dioxo-1-oxa-2-phospholanes cannot be obtained by ordinary distillation. In order to obtain very pure material by distillative treatment, it is essential that the distilling apparatus used should have the necessary separating power. The separating power of rectifying columns depends on the provision of a certain minimum number of trays, and also on the reflux ratio. These, however, are parameters which in fine purification work necessarily lead to an increased pressure difference between the base and head of the column.

Maintaining 2-methyl-2,5-dioxo-1-oxa-2-phospholane, i.e. the lowest-boiling of the present phospholanes, under a pressure increased merely by no more than several mm Hg results in an increase of the compound's boiling point to more than 200° C, i.e. to a temperature which is higher than the decomposition temperature. In other words, while it is possible for the present phospholanes to be expelled from mixtures containing them by distillative treatment as in the prior art, it is impossible for them to be finely purified by this treatment. The thermal decomposition of the phospholanes wherever it occurs in practice has adverse effects on the yield, and the resulting low-boiling cleavage products do affect the distillation vacuum to such an extent that the procedure is very likely to be disturbed.

We have now unexpectedly found that the 2,5-dioxo-1-oxa-2-phospholanes first specified herein can be purified in a distilling column having an appropriate number of separating trays disposed therein, provided that the boiling point of the respective phospholane is reduced, to the extent necessary for the phospholane to remain below its decomposition temperature, by reducing the pressure prevailing in the column and admixing the phospholane with one or more inert gases (as herein defined), e.g. nitrogen or air. An important feature of the present process provides for the various trays in the distilling column to be individually heatable, the uppermost tray being maintained at the lowest of the tray temperatures and the lowermost tray being maintained at the highest such temperature.

The distilling apparatus used in the process of the present invention does not call for the use of a still as used in the prior art. As a result, it is possible to avoid the long residence times which the material is liable to spend in the still, at high temperatures, in the priorart distilling methods. The heat necessary to evaporate the low-boiling impurities, which remain in the present distilling column for only a short period, is supplied through the individually heatable trays. The distilling apparatus used in the process of the present invention thus enables the crude phospholane to be freed from practically all low-boiling impurities contained in it except for a quite minor residual content. Hot crude phospholane thus freed from the low-boiling impurities is taken from an outlet below the lowermost tray in the column and delivered to a film evaporator to be distilled off, preferably by a short distillation path, from higher-boiling impurities.

According to the present invention, then, we provide a process for the distillative purification of a 2,5-dioxo-1-oxa-2-phospholane of the formula:

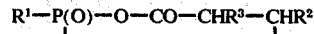

in which $R^1$ stands for an alkyl radical having 1, 2, 3 or 4 carbon atoms, or a phenyl radical, and $R^2$ and $R^3$ each stand for hydrogen or $CH_3$, which comprises: preheating the respective crude compound to 120° to 160° C and feeding it to the head of a distilling column provided with a plurality of individually heatable trays maintained at temperatures increasing (as herein defined) from the uppermost tray to the lowermost, the uppermost tray in the column being maintained at 120° to 160° C, preferably 125° to 140° C, and the lowermost tray being maintained at 160° to 200° C, preferably 170° to 190° C, the pressure at the head of the column being 20 to 200 mm Hg, preferably 50 to 120 mm Hg; introducing an inert gas (as herein defined) preheated to 160° to 200° C countercurrently at the base of the column; withdrawing overhead those impurities having a boiling point lower than that of the respective 2,5-dioxo-1-oxa-2-phospholane, together with the inert gas; withdrawing the 2,5-dioxo-1-2-phospholane thus freed from low-boiling impurities from the base of the distilling column and passing it to a film evaporator; and distilling off the 2,5-dioxo-1-oxa-2-phospholane from higher-boiling impurities in the film evaporator under a pressure of 0.1 to 5 mm Hg, preferably C.3 to 1 mm Hg.

Preferred features of the present invention provide:

a. for the proportion of inert gas introduced countercurrently as specified above to the 0.1 to 1 normal $m^3$ (i.e. $m^3$ at S.T.P.), preferably 0.2 to 0.6 normal $m^3$, per liter of liquid 2,5-dioxo-1-oxa-2-phospholane;

b. for the temperature at which the above-mentioned lowermost tray is maintained to be equivalent to the boiling point of the respective 2,5-dioxo-1-oxa-2-phospholane under the distilling conditions prevailing; and c. for the crude compound which is to be purified to be preheated to at least the temperature at which the above-mentioned uppermost tray is maintained, the inert gas introduced countercurrently to this crude compound being preheated to at least the temperature at which the above-mentioned lowermost tray is maintained.

The process of the present invention will now be described more fully with reference to the accompanying diagrammatic drawing, the single FIGURE of which is a view in vertical section of a preferred form of apparatus for use in carrying out this process.

In the apparatus shown in the drawing, the 2,5-dioxo-1-oxa-2-phospholane which is to be purified is introduced in liquid form, via a heated line 1 and a pre-heater 2, at a temperature of 120°–160°, into a distilling column 3. The column 3 is provided with individually heatable jacket segments and individually heatable perforated trays whereby there is established a temperature sequence increasing (as herein defined) from the head of the column down to its base. The necessary heat can be supplied indirectly by means of superheated steam or a liquid heat-transfer medium. More specifically, the heat is supplied so as to maintain a temperature of 120° to 160° C at the uppermost tray $a$ and a temperature of 160° to 200° C at the lowermost tray $j$. Placed between these two trays there are intermediate trays $b$ to $i$. The preheated crude phospholane is introduced at the head of the column, and a preheated inert gas (as herein defined), supplied through a line 7 and a pre-heater 8, is introduced, countercurrently with respect to the phospholane, at the base of the column 3; the inert gas should preferably be admitted to the column at a temperature equivalent to that of the liquid flowing down from the lowermost tray $J$. By operating the column 3 in this manner, the low-boiling impurities in the crude phospholane can be quantitatively removed together with the inert gas.

That portion of the phospholane which is carried out of the column 3 with the inert gas is condensed in a dephlegmator 4 placed above the head of the column 3, and is thereafter recycled to the column 3. A stream of inert gas and low-boiling impurities in vapour form is drawn off by means of a vacuum pump 6 which is so operated as to maintain a pressure of 20 to 200 mm Hg at the head of the column.

The phospholane freed from the low-boiling impurities flows from the lowermost tray $j$ to the outlet of the column 3, from which it is conveyed through a heated line 9 to the head of a thin-film evaporator 10, in which it is distilled off under a vacuum of approximately 1 mm Hg. The heat necessary to evaporate the phospholane is supplied by means of a heating jacket 13. The phospholane is liquefied on an internal condenser 5 and removed through a line 11, whereas higher-boiling impurities are removed by way of a separate outlet from the evaporator 10, and through a line 12.

Purified 2,5-dioxo-1-oxa-2-phospholanes are obtainable by the process of the present invention which are colourless and odourless liquids which solidify to white crystalline masses on cooling. Gas-chromatographic analysis has shown that these products can have a purity of more than 99.9 weight %, so that they are of a quality which makes them particularly suitable for condensation with polyester forming reactants.

In addition this, the nature of the present process is such as to permit the attainment of optimum yields even when scaled up to any commercially desirable extent.

The following Examples illustrate the invention; both of them employ an apparatus as described above with reference to the accompanying drawing.

EXAMPLE 1

Purification of 2-methyl-2,5-dioxo-1-oxa-2-phospholane.

6.2 kg/h of this phospholane in a crude form was preheated in the pre-heater 2° to 150° C, and conveyed through the heated line 1 to the uppermost tray $a$ of the ten individually heatable perforated trays $a$ to $j$ provided in the column 3. Trays $a$ and $b$ were heated to 130° C, trays $c$ and $d$ to 145° C, trays $e$ and $f$ to 150° C, trays $g$ and $h$ to 165° C, and trays $i$ and $j$ to 170° C. A reduced pressure of 50 to 100 mm Hg was maintained at the head of the column by means of the vacuum pump 6, and 1.5 normal $m^3/h$ of nitrogen preheated to 170° C was introduced through the line 7 and the preheater 8. A temperature of 100° C was established in the dephlegmator 4 mounted above the head of the column 3. Crude phospholane free from low-boiling impurities was found to accumulate at the base of the column 3, from which it was continuously metered through the line 9 to the thin-layer evaporator 10, in which the 2-methyl-2,5-dioxo-1-oxa-2-phospholane was distilled off at a temperature of 150° C under 0.5 mm Hg. 5.8 kg/h of the purified phospholane, corresponding to a yield of 97%, calculated on the phospholane in the crude starting material, was drawn off through the line 11. Specimens of the purified 2-methyl-2,5-dioxo-1-oxa-2-phospholane were tested by determining their melting point, which was 101° to 106° C. The impurities still present in the purified product were monitored by gas-chromatography. They comprised 100 to 500 ppm (parts per million).

EXAMPLE 2

Purification of 2-phenyl-2,5-dioxo-1-oxa-2-phospholane.

In the same apparatus as in Example 1, 8.15 kg/h of this phospholane in a crude form was preheated in the heater 2 to 160° C, and conveyed through the heated line 1 to the uppermost individually heatable perforated tray $a$ of the column 3. Trays $a$ and $b$ were heated to 135° C, trays $c$ and $d$ to 150° C, trays $e$ and $f$ to 165° C, trays $g$ and $h$ to 170° C, and trays $i$ and $j$ to 175° C.

1.5 normal $m^3/h$ of nitrogen preheated to 175° C was introduced into the apparatus through the line 7 and the preheater 8, a reduced pressure of 50 to 80 mm Hg being maintained at the head of the column 3 and a temperature of 90° C being established in the dephlegmator 4. In the thinfilm evaporator 10, the 2-phenyl-2,5-dioxo-1-oxa-2-phospholane was distilled off at 205° C under 0.3 mm Hg. 7.8 kg/h of the purified phospholane, corresponding to a yield of 97%, calculated on the phospholane in the crude starting material, was drawn off through the line 11. This purified product had a melting point of 87° C, and had a total impurity content of 100 to 300 ppm.

As will be appreciated from the references, in the above description, to nitrogen or air, the term "inert gas" is employed herein to denote any gas which is indifferent to the respective phospholane, and its impurities, under the relevant conditions.

Also, references herein to temperatures "increasing" from the uppermost tray to the lowermost are to be understood to mean that temperature increments occur between successive trays or groups of trays, in the downward direction, so that none of the trays is maintained at a temperature below that of the next tray above it; thus pairs of adjacent trays may have equal temperatures, as in the above Examples.

We claim:

1. A process for the distillative purification of a 2,5-dioxo-1-oxa-2-phospholane of the formula:

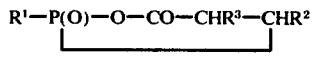

in which $R^1$ stands for an alkyl radical having from 1 to 4 carbon atoms, or a phenyl radical, and $R^2$ and $R^3$ each stand for hydrogen or $CH_3$, which comprises: preheating the respective crude compound to 120° to 160° C and feeding it to the head of a distilling column provided with a plurality of individually heatable trays maintained at temperatures increasing (as herein defined) from the uppermost tray to the lowermost, the uppermost tray in the column being maintained at 120° to 160° C and the lowermost tray being maintained at 160° to 200° C, the pressure at the head of the column being 20 to 200 mm Hg; introducing an inert gas (as herein defined) preheated to 160° to 200° C countercurrently at the base of the column; withdrawing overhead those impurities having a boiling point lower than that of the respective 2,5-dioxo-1-oxa-2-phospholane, together with the inert gas; withdrawing the 2,5-dioxo-1-oxa-2-phospholane thus freed from low-boiling impurities from the base of the distilling column and passing it to a film evaporator; and distilling off the 2,5-dioxo-1-oxa-2-phospholane from higher boiling impurities in the film evaporator under a pressure of 0.1 to 5 mm Hg.

2. A process as claimed in claim 1, wherein the proportion of inert gas introduced countercurrently as specified in claim 1 is 0.1 to 1 normal $m^3$ per liter of liquid 2,5-dioxo-1-oxa-2-phospholane.

3. A process as claimed in claim 1, wherein the temperature at which the said lowermost tray is maintained is equivalent to the boiling point of the respective 2,5-dioxo-1-oxa-2-phospholane under the distilling conditions prevailing.

4. A process as claimed in claim 1, wherein the crude compound which is to be purified is preheated to at least the temperature at which the said uppermost tray is maintained, and the inert gas introduced countercurrently to the crude compound is preheated to at least the temperature at which the said lowermost tray is maintained.

* * * * *